United States Patent [19]

Vieira et al.

[11] 4,322,683
[45] Mar. 30, 1982

[54] CONTROL APPARATUS FOR EDDY CURRENT NON-DESTRUCTIVE TESTING USING A DIGITAL COMPENSATING CIRCUIT

[75] Inventors: David D. Vieira, Puyricard; Jacques Dinard, Manosque; Alain Stössel, Aix en Provence, all of France

[73] Assignee: Commissariat a l'Energie Atomique, Paris, France

[21] Appl. No.: 126,364

[22] Filed: Mar. 3, 1980

[30] Foreign Application Priority Data

Mar. 9, 1979 [FR] France ................................ 79 06149

[51] Int. Cl.³ ........................ G01R 33/12; G01N 27/90
[52] U.S. Cl. .................................... 324/225; 324/233; 324/240
[58] Field of Search ................ 324/233, 225, 236–241, 324/228, 202

[56] References Cited

U.S. PATENT DOCUMENTS

| | | | |
|---|---|---|---|
| 3,229,198 | 1/1966 | Libby | 324/233 |
| 3,337,796 | 8/1967 | Hentschel et al. | 324/233 |
| 4,059,795 | 11/1977 | Mordwinkin | 324/233 |
| 4,084,136 | 4/1978 | Libby et al. | 324/238 |
| 4,207,520 | 6/1980 | Flora et al. | 324/233 X |
| 4,230,987 | 10/1980 | Mordwinkin | 324/233 X |

FOREIGN PATENT DOCUMENTS

| | | | |
|---|---|---|---|
| 1335569 | 7/1963 | France | |
| 2010781 | 2/1970 | France | |
| 2031153 | 4/1980 | United Kingdom | 324/233 |

*Primary Examiner*—Gerard R. Strecker

[57] ABSTRACT

Digital apparatus for controlling members by eddy currents comprising a sensor constituted by a primary winding and a secondary winding, an exciting sinusoidal voltage generator, a correcting circuit for eliminating the residual voltage supply by the secondary winding of the sensor, a circuit for analyzing the corrected measuring voltage incorporating two samplers and a means for displaying the two signals supplied by the two samplers. The exciting voltage generator is of the digital type and comprises an oscillator, a counter, a memory and a digital-analog converter. The collection circuit comprises a number selection means, a comparator, a counter, a memory and a digital-analog converter. The means for generating control pulses for the samplers comprises a number selection means, a comparator and a digital phase shifter.

A particular application is in the field of non-destructive testing.

5 Claims, 3 Drawing Figures

CONTROL APPARATUS FOR EDDY CURRENT NON-DESTRUCTIVE TESTING USING A DIGITAL COMPENSATING CIRCUIT

BACKGROUND OF THE INVENTION

The present invention relates to a digital apparatus for controlling members by eddy currents and it can be used in non-destructive control processes.

It is known that the control of a metal member by eddy currents involves the study of the variations of the currents induced in said member by the magnetic field of a primary winding traversed by an alternating exciting current. On their return, these induced currents produce a field which opposes the induction field and which acts on the impedance of a secondary winding. The assembly of the primary and secondary windings forms the sensor in which or in front of which is displaced the member to be controlled. Any defect or fault in the latter occurring at the level of the sensor (change of dimension, variation in the electrical conductivity, variation in the magnetic permeability, cracks, etc) modifies the phase and intensity of the eddy currents and correlatively changes the impedance of the secondary winding.

For sensitivity reasons, the receiving coil is constituted by two secondary windings connected in opposition in such a way that the measuring signal is the asymmetrical voltage of the two windings. The measurement is differential if the two windings examine two adjacent zones of the member to be controlled and is absolute if only one of the two windings is in the presence of said member (the secondary winding then has a reference standard member). The voltage supplied by the sensor is amplified and then analysed in its resistive (or true) component X and in its reactive (or imaginary) component Y. The alternating voltage supplied by the sensor is then represented on the screen of a cathode tube by a point of cartesian coordinates X and Y.

Due to the slight asymmetries between the two parts of the secondary winding, even when there is no fault in the member to be controlled, the sensor supplies a residual voltage which may falsify the measurement. Thus, an attempt is made to eliminate this residual voltage by means of an auxiliary correcting or compensating circuit comprising on the one hand a compensating voltage generator, whose frequency is equal to that of the exciting voltage and whose amplitude and phase are regulatable and on the other hand a differential amplifier with two inputs, one receiving the compensating voltage and the other the voltage supplied by the sensor. The regulation of the amplitude and phase of the compensating voltage is carried out in such a way that in the presence of a member which is considered to be satisfactory, the amplifier supplies a zero voltage, at least at the exciting frequency. It is this corrected voltage which is finally analysed. To this end, a circuit is used, which generally comprises two periodic samplers both of which operate at the frequency of the exciting voltage, but in quadrature with respect to one another. These samplers receive a control pulse from the exciting voltage generator, said pulse passing along a delay line, thus permitting the regulation of the sampling times.

Finally, it is standard practice in such apparatuses to provide a means for rotating the measurement points displayed on the cathode tube screen. In general, this means consists of circuits able to calculate quantities of the form $X \cos \theta - Y \sin \theta$ and $X \sin \theta + Y \cos \theta$, $\theta$ being the desired rotation angle.

In connection with said special means and apparatus, reference can be made to U.S. Pat. No. 3,229,198 of H. L. LIBBY, granted on Jan. 11, 1966 and entitled "Eddy current nondestructive testing device for measuring multiple parameter variables of a metal sample".

BRIEF SUMMARY OF THE INVENTION

The present invention relates to an apparatus of this type. However, it is designed to operate in preferred manner in a low or very low frequency range of approximately 1 Hz to approximately 3 kHz. This range corresponds to two fields of application, the second being more important than the first:

(1) Control of non-magnetic materials:

Used at the highest frequencies of the range (starting from about 1 kHz) the apparatus according to the invention permits the control of the satisfactory state (i.e. the detection of point defects) of non-magnetic products having a high electrical conductivity. These products can be in the form of tubes, bars, sections and optionally plates. On the same materials, it is also possible to check certain dimensional parameters and particularly thicknesses, when the latter are relatively large (several millimeters).

(2) Control of magnetic materials

The majority of the applications for the apparatus according to the invention relates to structural characteristics of magnetic materials. In this case, the measurement is still absolute and comparative, the apparatus being calibrated relative to a reference member. The measurement can be carried out either with two sensors, one of them receiving a reference member, or with a single sensor incorporating two secondary windings, wound in the opposite direction to one another and whereof only one is directly in the presence of the member to be controlled.

The apparatus according to the invention makes it possible to solve the following control problems: Sorting or classifying of materials and more specifically variations in them: the apparatus making it possible to detect differences in the chemical composition.

Control of heat treatments such as annealing, tempering, etc.

Control of mechanical states: evaluation of cold-working levels.

Correlation with mechanical properties, such as hardness.

It is pointed out that this list is naturally non-limitative.

This particular operating mode of the apparatus according to the invention (at low frequency and in absolute mode) necessitates maximum frequency stability, both at the level of the exciting voltage of the sensor and of the correcting and sampling means for the signal supplied by the sensor. However, the prior art means do not make it possible to obtain this high level of stability.

The present invention obviates this disadvantage by proposing a digital or numerical version of the means indicated hereinbefore able to give the requisite stability to the apparatus. In addition to this vital advantage there are others linked with an increase in the quality of analysis, an improvement to the reproducibility of the measurements, the possibility of carrying out very precise calibrations and finally the way in which the measuring signal is oriented.

All these advantages are obtained by a special design of the exciting voltage generator, the correcting circuit and the control means for the samplers.

More specifically, the present invention relates to a control apparatus utilizing eddy currents and comprising:

a sensor constituted by a primary winding and a secondary winding, a sinusoidal exciting voltage generator having a given frequency F, said generator supplying the primary winding, a correcting circuit for eliminating the residual voltage supplied by the secondary winding of the sensor, said circuit comprising a compensating voltage generator at frequency F for the exciting voltage and having a regulatable amplitude and phase and a differential amplifier having two inputs, one receiving the compensating voltage and the other the voltage supplied by the sensor and one output supplying a corrected measuring voltage, a circuit for analysing the correct measuring voltage said circuit comprising two samplers operating at the frequency of the generator and in phase quadrature with respect to one another, said samplers being controlled by pulses processed by an appropriate means connected to the generator, means for displaying the two signals supplied by the two samplers, wherein:

(A) the exciting voltage generator is of the digital type and comprises an oscillator transmitting pulses at a stabilised frequency Fs, a first counter of maximum capacity C connected to the oscillator, a first memory containing a Table of C digital values of the sine function, said memory being addressed by the counter content, a first digital-analog converter connected to the memory, said converter supplying a sinusoidal voltage of frequency $F = Fs/C$ which is applied to the primary winding, (B) the correcting circuit comprises:
   (i)—a first regulatable means for selecting a number being between 0 and C, a first comparator with two inputs, one connected to said first means and the other to the output of the first counter of the generator, and an output supplying a pulse when the numbers received by the two inputs are equal,
   (ii)—a second counter identical to the first, said counter receiving the pulses supplied by the oscillator of the digital generator and having a zeroing input connected to the output of the first comparator,
   (iii)—a second memory containing a Table of C digital values of the sine function, said memory being addressed by the content of the second counter, a second digital-analog converter connected to the memory and a regulatable potentiometer connected to the output of the converter, (C) the means for generating the control pulses of the samplers comprises:
   (i)—a second means for selecting a number between o and C, a second digital comparator with two inputs, one connected to said second means and the other to the first counter of the generator and an output supplying a pulse when the two numbers received by the inputs are equal, said output being directly connected to one of the samplers,
   (ii)—a digital phase shifter constituting a third counter connected to the oscillator of the digital generator, said third counter having a zeroing input which is connected to the output of the second comparator and having a maximum capacity equal to C/4 and having an output which supplies a pulse when its content reaches the maximum capacity C/4, said output being connected to the other sampler.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
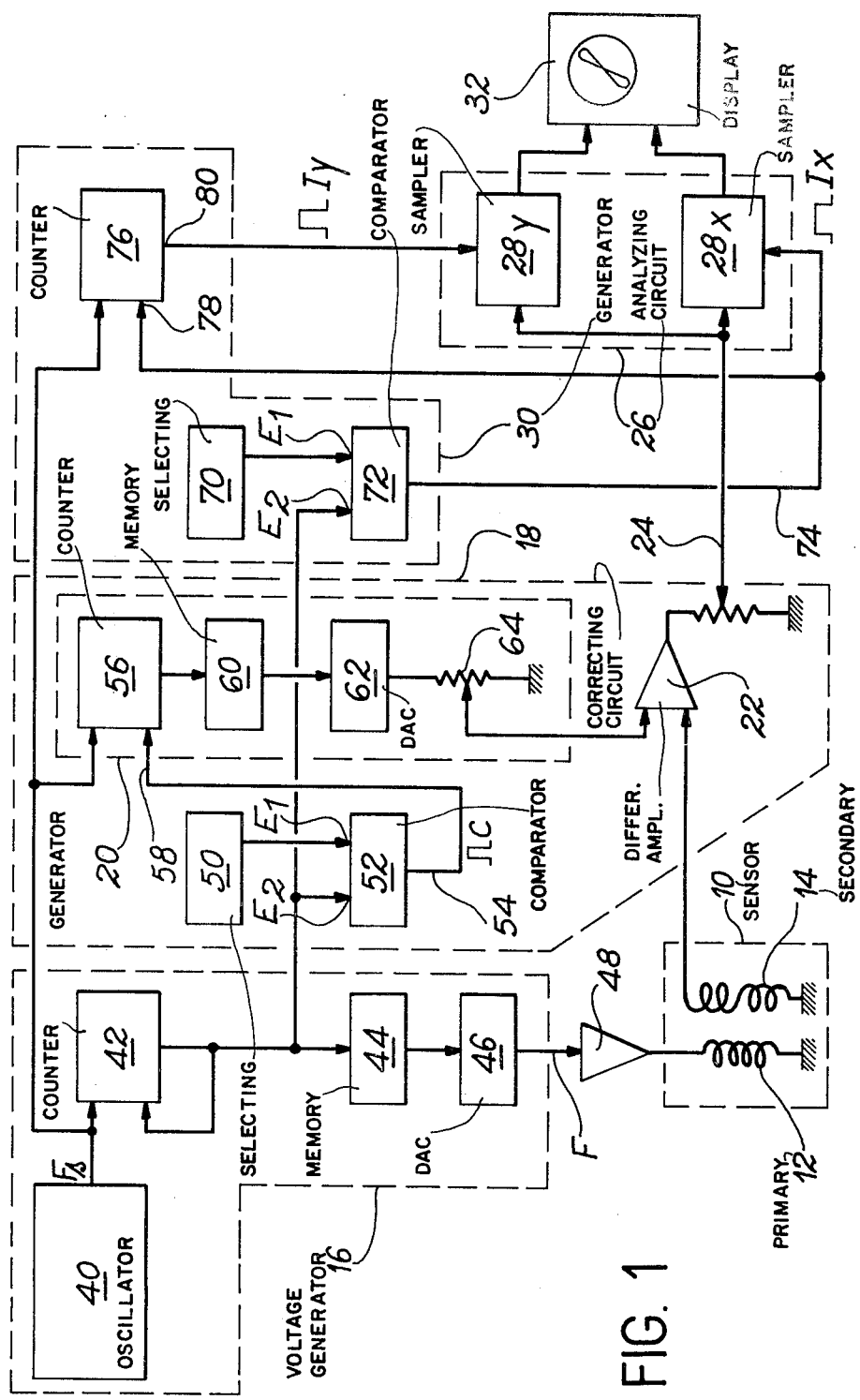
FIG. 1 the synoptic diagram of the apparatus according to the invention.

The apparatus shown in FIG. 1 comprises:

a sensor 10 constituted by a primary winding 12 and a secondary winding 14, the latter incorporating two parts connected in series and in opposition, a sinusoidal voltage generator 16 for exciting the primary winding at a frequency F, a correcting circuit 18 for eliminating the residual voltage supplied by the secondary winding 14 of the sensor, said circuit 18 incorporating a generator 20 for the compensating voltage at frequency F of the exciting voltage and having a regulatable amplitude and phase, and a differential amplifier 22 with two inputs, one receiving the compensating voltage and the other the voltage supplied by the sensor 10, and an output 24 supplying a corrected measuring voltage, a circuit 26 for analysing the corrected measuring voltage supplied by amplifier 22, said circuit comprising two samplers 28X and 28Y, both operating at the frequency F of the generator, but in phase quadrature with respect to one another, said samplers being controlled by pulses processed by a means 30 connected to the generator 16, means 32 for displaying the two signals supplied by the two samplers 28X and 28Y.

The same construction is used in the prior art apparatus. However, the apparatus according to the invention also has the following novel features:

(A) the exciting generator, (B) the correcting circuit and (C) the control of the samplers. These features are defined below:

(A) the exciting voltage generator 16 is of the digital type and comprises an oscillator 40 transmitting pulses at a frequency Fs, a first counter 42 having a maximum capacity C connected to the oscillator 40, a first memory 44 containing a table of C digital values for the sine function, said memory being addressed by the content of counter 42 and a first digital-analog converter 46 connected to the memory 44, said converter supplying a sinusoidal voltage amplified by a circuit 48, then applied to the primary winding;

(B) a correcting circuit 18 comprises:
   (i)—a first regulatable means 50 for selecting a number between 0 and C, a first comparator 52 with two inputs $E_1$ and $E_2$, the first connected to means 50 and the second to the output of the first counter 42 for generator 16, said comparator having an output 54 supplying a pulse when the numbers received by the two inputs $E_1$ and $E_2$ are equal, (ii)—a first counter 56, identical to counter 42, said counter 56 receiving pulses supplied by the oscillator 40 located in the digital generator 16, said comparator having a zeroing input 58 connected to the output 54 of the first comparator 52, (iii)—a second memory 60 containing a table of C digital values of the sine function, said memory being addressed by the content of the second counter 56, a second digital-analog converter 62 connected to memory 60 and a regulatable potentiometer connected to the output of converter 62, (C) the means 30 for producing the control pulses of samplers 28X and 28Y comprises:

(i)—a second regulatable means 70 for selecting a number between 0 and C, a second digital comparator 72 with two inputs $E_1$ and $E_2$, the first connected to means 70 and the second to counter 42 of generator 16, and an output 74 supplying a pulse IX when the two numbers received at the inputs $E_1$ and $E_2$ are equal, said output being directly connected to sampler 28X, (ii)—a third counter 76 connected to the oscillator 40 of the digital generator 16, said third counter having a zeroing input 78 which is connected to the output 74 of the second comparator 72, offering a maximum capacity equal to C/4, whilst its output 80 supplies a pulse IY when the content reaches the maximum capacity C/4, said output being connected to the sampler 28Y.

For the purposes of describing this circuit, it will be assumed that the capacity C of counters 42 and 56 is equal to 512.

The operation of generator 16 is as follows. The memory 44 has 512 points of 8 binary elements, making it possible to code a complete sine curve cycle with 512 addresses. These 512 addresses are supplied by counter 42 which has ten stages, the 9 first stages giving said addresses ($2^9 = 512$) and the tenth permitting the zeroing of the counter. Thus, a sine curve cycle is obtained when 512 pulses have been transmitted by oscillator 40. If Fs is the frequency of these pulses, the frequency F of the sine curve signal supplied by memory 44 is equal to Fs/512.

For information purposes, memory 44 can be of the REPROM type (Reprogrammable read only memory) and is for example constituted by the IM 6604 circuit marketed by INTERSIL.

The digital-analog converter 46 operates with an input code having at least 8 binary elements. It is possible to use commercially available converters with 12 binary elements, the four lower weight binary elements being at logic level 1.

If the output signal of the converter is in current, a regulatable current-voltage converter is added. The circuit, e.g. DAS 1285 of the National Semiconductors Company contains such a digital-analog converter and a current-voltage converter.

The correspondence between the binary input code and the output voltage varying between $+V$ and $-V$ can finally be as follows:

| Code: | 11 111 111 | 11 111 110 | 01 111 111 | 00 000 000 |
|---|---|---|---|---|
| Voltage: | $-V$ | $-V + \epsilon$ | 0 | $+V - \epsilon$ |

As amplifier 48 does not form part of the invention, it will not be described here. It is merely pointed out that it can be an operational amplifier, for example type ICH 8520 of the Intersil company.

The correcting circuit firstly comprises a voltage generator 20, whose operation is identical to that described hereinbefore, because it comprises a counter 56, memory 60 and converter 62 identical to the counter 42, memory 42 and converter 46. However, this circuit also contains a digital phase shifter which operates in the following manner.

The origin of the phases can be considered as the time of zero resetting of counter 42. At its inputs $E_1$ and $E_2$ comparator 52 receives two numbers $N_1$ and $N_2$, the first being fixed and determined by means 50, the second being variable and progressing from 0 to 511 with the content of counter 42. When $N_2$ reaches $N_1$ the output of comparator 52 changes state and a pulse Ic appears on the connection 54. This pulse is perfectly introduced into the cycle of 512 points transmitted by oscillator 40. Its position can be adjusted by varying the selected number $N_1$ between 0 and 511. This pulse is used for the zeroing of counter 56 and the zero resetting time fixes the start and therefore the phase of the sine curve constituting the correcting signal.

The 512 points of a cycle thus correspond to a possibility of varying by 360° the phase displacement of the correcting voltage compared with the exciting voltage. The phase displacement expressed in degrees is therefore equal to $360.N_1/512$.

The control circuit 30 of the samplers functions as follows. The control pulse IX of sampler 28X is produced in exactly the same way as pulse Ic for determining the phase of the correcting signal. The assembly of means 70 and comparator 72 is the same as the assembly of means 50 and comparator 52 described hereinbefore.

The control pulse IY of sampler 28Y must be phase-displaced by a quarter of a cycle compared with pulse IX. To this end, pulse IX is addressed to the zeroing input of counter 76, whose capacity is equal to $512/4 = 128$. This pulse determines the starting time of the count in counter 76. The passage to 128 of said counter controls the transmission of output 80 of a pulse which is displaced by 128 points compared with the zeroing pulse, i.e. by a quarter of a cycle. This pulse thus constitutes the pulse IY necessary for the control of sampler 28Y.

It can be seen that control circuit 30 not only makes it possible to produce the pulses necessary for the control of the samplers, but also permits the orientation of the signal appearing on the display screen. This orientation is obtained by modifying the number $N_1$ selected by means 70. This arrangement also has the following advantage. If the measuring signal has a distortion due to a non-linearity of the magnetic properties of the material inquestion (for sufficiently high exciting amplitudes) it may be of interest to analyse a particular zone of the measuring signal. The apparatus according to the invention permits this due to the regulation of the position of pulse IX and correlatively of pulse IY. The choice of position of the sampling signals then becomes a supplementary element of analysis.

Figure 2:
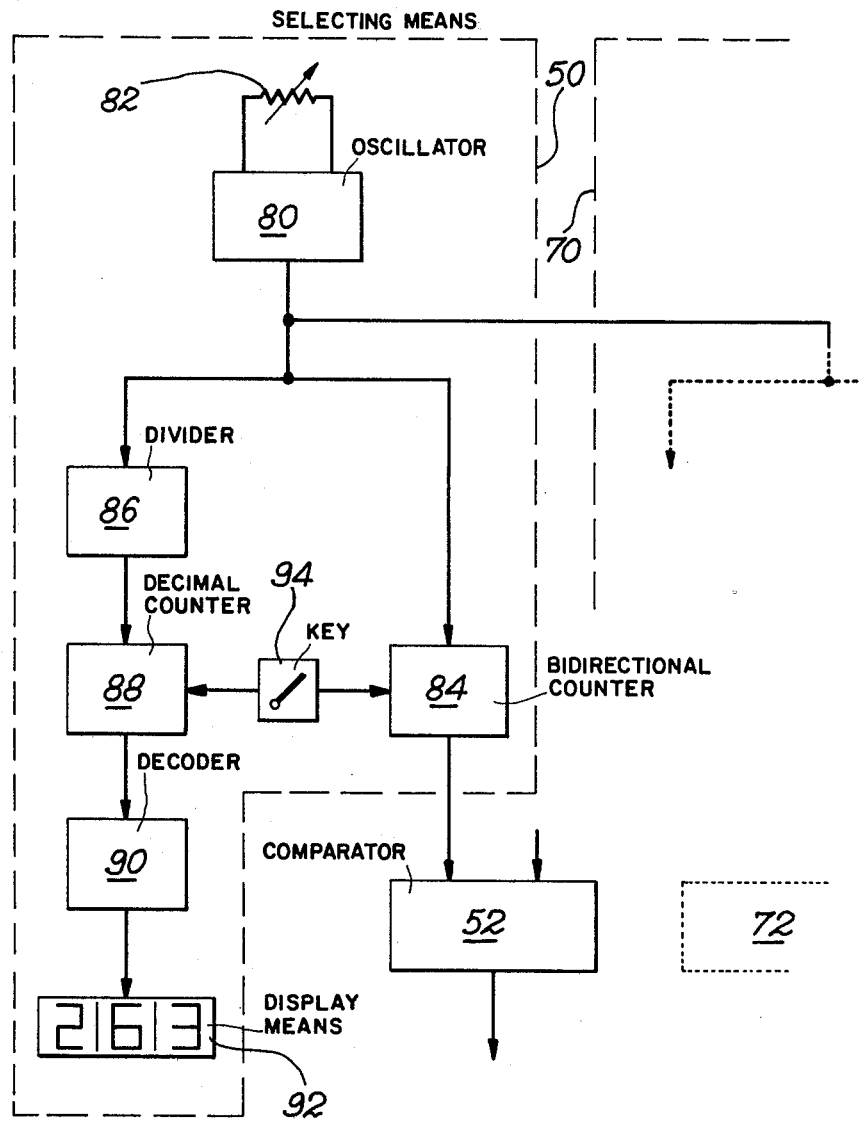
FIG. 2 a special embodiment of the means for the formation and display of a phase displacement of the sampling control pulses.

FIG. 2 shows a special embodiment of means 50 and 70, for selecting a number $N_1$ between 0 and C. The means shown in the drawing comprises an astable oscillator 80 having a time constant regulatable by means of a variable resistor 82, a bidirectional counter 84 connected to the oscillator, a divider 86 by C/360 followed by a decimal counter 88 connected to a circuit 90 for the decoding and control of a display means 92, for example with 7 segments. The bidirectional counters are controlled by a key 94 having three positions: forward count-stop-backward count. The output of the bidirectional counter 84 is applied to the input $E_1$ of a comparator (comparator 52 or 72 of FIG. 1).

For an operation based on a cycle with 512 points divider 86 supplies 260 output pulses for 512 input pulses. Each of these pulses therefore represents 0.7 angular degrees. These pulses are added in the bidirectional counter 88, whose content is displayed by means 92. The desired number $N_1$ is obtained by placing key 94 on the forward counting position (or if applicable on the backward counting position) in order to increase (or decrease) the summated number up to the obtension of the desired number, which is then directly displayed in degrees by means 92.

Naturally, if means 70 is identical to means 50 a single astable oscillator 80 can be used for these two means.

Figure 3:
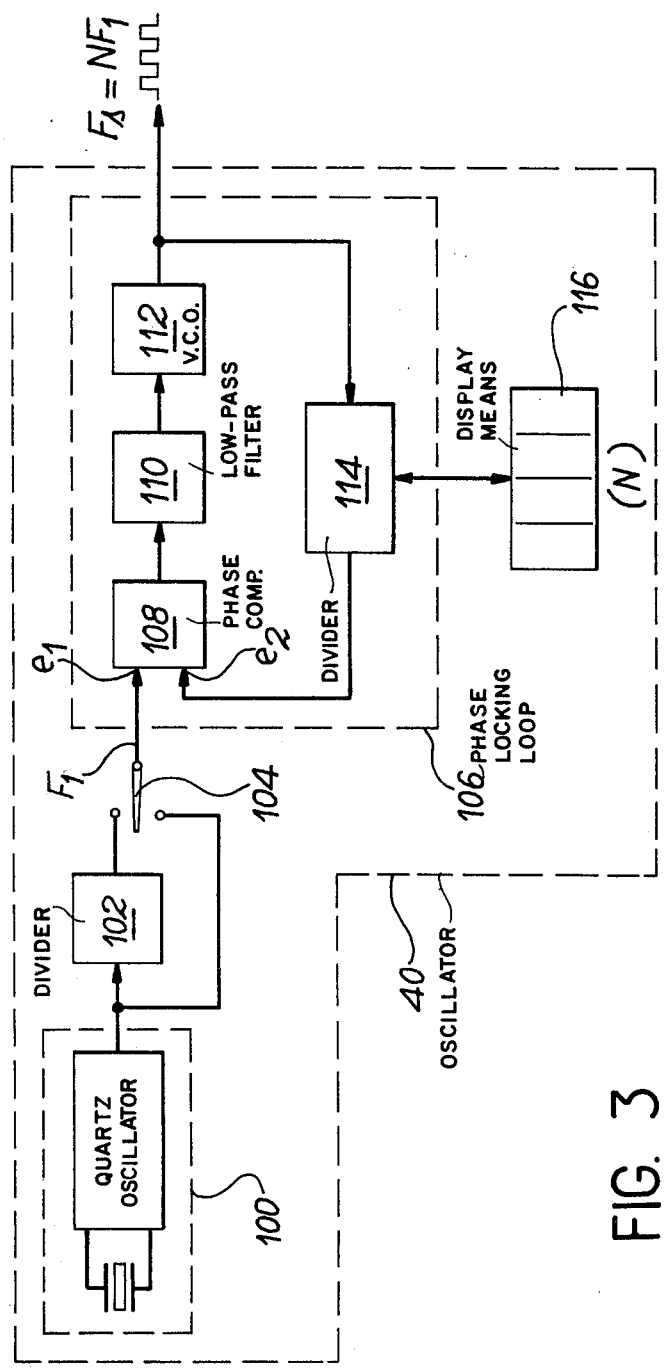
FIG. 3 a special embodiment of the digital generator.

FIG. 3 shows a special embodiment of the oscillator 40 supplying pulses at the stabilised frequency Fs. The circuit shown in the drawing comprises:

(i)—an assembly 100 constituted by a quartz oscillator and a counter, a divided 102 by ten and a switch 104, said assembly supplying pulses at a frequency $F_1$;

(ii)—a phase locking loop 106 incorporating in conventional manner a phase comparator 108 with two inputs $E_1$ and $E_2$, the first receiving the pulses at frequency $F_1$, a low-pass filter 110 connected to phase comparator 108, a voltage control oscillator 112 connected to filter 110, the output of said oscillator being brought to the second input $E_2$ of phase comparator 108 across a divider regulatable by a number N and associated with a display means 116 for the number N.

This signal consequently has a frequency $F_2$. The output of oscillator 40 supplies pulses at frequency Fs.

This circuit operates in a conventional manner. Frequency $F_1$ determined by the oscillator-counter 100 constitutes a reference. When the frequency $F_2$ of the signal reinjected at input $E_2$ of phase comparator 108 differs from the reference frequency applied to input $E_1$, the phase comparator produces an error signal which is applied to oscillator 112 which corrects its frequency until $F_1$ and $F_2$ are identical. Due to the presence of the divider 114 by N in a balance state one has $F_1=F_2=Fs/N$, i.e. $Fs=NF_1$. Thus, it is possible to obtain a very stable frequency Fs and which is at the same time regulatable by acting on divider 114.

For illustrative purposes, the phase locking loop 108 can be constituted by circuit type 4046 of the R.C.A. Company, whilst the divider can be circuit 4059 of the same company, said circuit being a programmable divider with coding wheels, N is then the division factor displayed by the coding wheels.

It should be noted that if C designates the capacity of counter 42, which receives and counts the pulses transmitted at frequency $Fs=NF_1$ by oscillator 40, the frequency F of generator 16 is equal to $Fs/C$, i.e. $NF_1/C$.

If the quartz oscillator frequency $F_1$ is taken to be a frequency in Hertz equal to capacity C (or C/10), the frequency F of the exciting generator, also expressed in Hertz, is equal to the division factor N (or N/10). This frequency then appears directly on the display means 116.

What is claimed is:

1. A control apparatus utilizing eddy currents and comprising:

a sensor contituted by a primary winding and a secondary winding, a sinusoidal exciting voltage generator having a given frequency F, said generator supplying the primary winding, a correcting circuit for eliminating the residual voltage supplied by the secondary winding of the sensor, said circuit comprising a compensating voltage generator having an output delivering a compensating voltage at frequency F of the exciting voltage and having a regulatable amplitude and phase, and a differential amplifier having two inputs, one receiving the compensating voltage and the other the voltage supplied by the sensor and one output supplying a corrected measuring voltage, a circuit for analyzing the corrected measuring voltage, said circuit comprising two samplers operating at the frequency of the generator and in phase quadrature with respect to one another, said samplers being controlled by pulses processed by an appropriate means connected to the generator, said samplers having each an input connected to said output of said differential amplifier, means for displaying the two signals supplied by the two samplers, wherein:

(A) the exciting voltage generator is of the digital type and comprises an oscillator transmitting pulses at a stabilised frequency Fs, a first counter of maximum capacity C connected to the oscillator, a first memory containing a Table of C digital values of the sine function, said memory being addressed by the counter content, a first digital-analog converter connected to the memory, said converter supplying a sinusoidal voltage of frequency $F=Fs/C$ which is applied to the primary winding, (B) the correcting circuit comprises:

(i)—a first regulatable means for selecting a number between 0 and C, a first comparator with two inputs, one connected to said first means and the other to the output of the first counter of the generator, and an output supplying a pulse when the numbers received by the two inputs are equal, (ii)—a second counter identical to the first, said counter receiving the pulses supplied by the oscillator of the digital generator and having a zeroing input connected to the output of the first comparator, (iii)—a second memory containing a Table of C of digital values of the sine function, said memory being addressed by the content of the second counter, a second digital-analog converter connected to the memory and a regulatable potentiometer having an input connected to the output of the converter and an output which is said output of said compensating voltage generator and which is connected to one input of said differential amplifier, (C) the means for generating the control pulses of the samplers comprises:

(i)—a second means for selecting a number between 0 and C, a second comparator with two inputs, one connected to said second means and the other to the first counter of the generator and an output supplying a pulse when the two numbers received by the inputs are equal, said output being directly connected to one of the samplers.

2. An apparatus according to claim 1, wherein the first and second regulatable means for selecting a number between 0 and C incorporate an astable oscillator having a manually regulatable time constant and a bidirectional counter connected to the said oscillator for each means.

3. An apparatus according to claim 2, wherein said first and second means for selecting a number between 0 and C also incorporates a display means having a divider by C/360 connected to the astable oscillator, followed by a decimal counter controlling a display.

4. An apparatus according to claim 1, wherein the oscillator transmitting the pulses at stabilized frequency Fs comprises:

(i)—a quartz oscillator associated with a counter and optionally a divider by 10, the assembly supplying pulses at a frequency $F_1$, (ii)—a phase locking loop incorporating a phase comparator with two inputs, the first receiving the pulses at frequency $F_1$, a low-pass filter connected to the phase comparator, a voltage controlled oscillator controlled by said filter, the output of the oscillator being brought to the second input of the phase comparator through a divider regulatable by a number N, said output then supplying pulses at frequency $Fs = NF_1$.

5. An apparatus according to claim 4, wherein the frequency $F_1$ of the quartz oscillator, expressed in Hertz, is equal to the maximum capacity C of the first counter (or to C/10) the frequency F of the pulses transmitted by the generator then being equal to N (or to N/10) and wherein the divided by N comprises a display means for the number N which then directly gives the frequency N of the generator.

* * * * *